United States Patent

Dickerson et al.

Patent Number: 5,871,892
Date of Patent: Feb. 16, 1999

[54] PORTAL RADIOGRAPHIC IMAGING

[75] Inventors: Robert E. Dickerson, Hamlin; Arthur G. Haus, Rochester; Kenneth E. Huff, Spencerport, all of N.Y.

[73] Assignee: Eastman Kodak Company, Rochester, N.Y.

[21] Appl. No.: 787,035

[22] Filed: Jan. 28, 1997

Related U.S. Application Data

[63] Continuation-in-part of Ser. No. 598,489, Feb. 12, 1996, abandoned.

[51] Int. Cl.$^6$ .................................. G03C 5/17; G03C 1/76
[52] U.S. Cl. .......................... 430/502; 430/139; 430/403; 430/506; 430/567; 430/966
[58] Field of Search .................................. 430/139, 966, 430/403, 502, 567, 604, 506

[56] References Cited

U.S. PATENT DOCUMENTS

| | | | |
|---|---|---|---|
| 4,414,310 | 11/1983 | Daubendiek et al. | 430/567 |
| 4,425,425 | 1/1984 | Abbott et al. | 430/502 |
| 4,425,426 | 1/1984 | Abbott et al. | 430/502 |
| 4,707,435 | 11/1987 | Lyons et al. | 430/494 |
| 4,803,150 | 2/1989 | Dickerson et al. | 430/502 |
| 4,868,399 | 9/1989 | Sephton . | |
| 4,900,652 | 2/1990 | Dickerson et al. | 430/502 |
| 4,997,750 | 3/1991 | Dickerson et al. | 430/509 |
| 5,252,442 | 10/1993 | Tsaur et al. | 430/502 |
| 5,449,599 | 9/1995 | Heremans | 430/567 |
| 5,455,139 | 10/1995 | Wada et al. | 430/139 |

OTHER PUBLICATIONS

Research Disclosure, vol. 184, Aug. 1979, Item 18431.

*Primary Examiner*—Thorl Chea
*Attorney, Agent, or Firm*—Carl O. Thomas

[57] ABSTRACT

Radiographic elements useful for therapy imaging are disclosed each comprised of a film support having first and second major surfaces and capable of transmitting radiation to which the radiographic element is responsive and, coated on both of the major surfaces, processing solution permeable hydrophilic colloid layers which are fully forehardened and limited to less than 45 mg/dm$^2$ of hydrophilic colloid to facilitate processing in less than 45 seconds, at least one of said layers on each major surface including light-sensitive silver halide grains capable of providing a contrast in the range of from 4 to 8 and containing less than 3 mole percent iodide, based on silver, the hydrophilic colloid layers allowing at least 30 percent crossover within a spectral region within which the silver halide grains are light-sensitive. The radiographic elements are useful for either in localization or verification imaging.

23 Claims, No Drawings

PORTAL RADIOGRAPHIC IMAGING

This is a continuation-in-part of U.S. Ser. No. 08/598,489, filed Feb. 12, 1996, now abandoned.

FIELD OF THE INVENTION

The invention is directed to portal radiography with radiation therapy treatment beams and, more specifically, to silver halide radiographic elements and intensifying screens for use in portal radiography.

DEFINITION OF TERMS

The term "RAD" is used to indicate a unit dose of absorbed radiation: an energy absorption of 100 ergs per gram of tissue.

The term "portal" is used to indicate radiographic imaging, films and intensifying screens applied to megavoltage radiotherapy conducted through an opening or port in a radiation shield.

The term "localization" refers to portal imaging that is used to locate the port in relation to the surrounding anatomy of the patient. Typically exposure times range from 1 to 10 seconds.

The term "verification" refers to portal imaging that is used to record patient exposure through the port during radiotherapy. Typically exposure times range from 30 to 300 seconds.

The term "contrast" as herein employed indicates the average contrast (also referred to as γ) derived from a characteristic curve of a portal radiographic element using as a first reference point (1) a density ($D_1$) of 0.25 above minimum density and as a second reference point (2) a density ($D_2$) of 2.0 above minimum density, where contrast is AD (i.e. 1.75)÷$\Delta\log_{10}E$ ($\log_{10}E_2 - \log_{10}E_1$), $E_1$ and $E_2$ being the exposure levels at the reference points (1) and (2).

The term "dual-coated" is employed to indicate radiographic elements having image forming layer units coated on opposite sides of a support.

The term "crossover" as herein employed refers to the percentage of light emitted by a fluorescent intensifying screen that strikes a dual-coated radiographic film and passes through its support to reach the image forming layer unit coated on the opposite side of the support.

The terms "kVp" and "MVp" stand for peak voltage applied to an X-ray tube X $10^3$ and $10^6$, respectively.

The term "fluorescent intensifying screen" refers to a screen that absorbs X-radiation and emits light.

The term "metal intensifying screen" refers to a metal screen that absorbs MVp level X-radiation to release electrons and absorbs electrons that have been generated by X-radiation prior to reaching the screen.

The terms "front" and "back" refer to features or elements nearer to and farther from, respectively, the X-radiation source than the support of the radiographic element.

The term "fully forehardened" is employed to indicate the forehardening of hydrophilic colloid layers to a level that limits the weight gain of a portal radiographic element to less than 120 percent of its original (dry) weight in the course of processing (see Examples below for reference process). The weight gain is almost entirely attributable to the ingestion of water during processing.

The term "rapid access processing" is employed to indicate dry-to-dry processing of a radiographic element in 45 seconds or less. That is, 45 seconds or less elapse from the time a dry imagewise exposed radiographic element enters a processor until it emerges as a dry, fully processed element.

All references to silver halide grains and emulsions containing two or more halides name the halides in order of ascending concentrations.

The "aspect ratio" of a grain is the ratio of its equivalent circular diameter (ECD) to its thickness. The ECD of a grain is the diameter of a circle having an area equal to the projected area of the grain.

The "coefficient of variation" (COV) of grain size (ECD) is defined as 100 times the standard deviation of grain size divided by mean grain size.

The term "covering power" is used to indicate 100 times maximum density divided by silver coating coverage measured in $g/dm^2$.

The term "colder" in referring to image tone is used to mean an image tone that has a more negative CIELAB b* value measured at a density of 1.0 above minimum density, where an optimally "cold" image tone is −6.5 or more negative. Measurement technique is described by Billmeyer and Saltzman, Principles of Color Technology, 2nd Ed., Wiley, New York, 1981, at Chapter 3. The b* values describe the yellowness vs. blueness of an image with more positive values indicating a tendency toward greater yellowness (image warmth).

The term "rare earth" is used to indicate elements having an atomic number of 39 or 57 through 71.

*Research Disclosure* is published by Kenneth Mason Publications, Ltd., Dudley House, 12 North St., Emsworth, Hampshire P010 7DQ, England.

BACKGROUND

In conventional medical diagnostic imaging the object is to obtain an image of a patient's internal anatomy with as little X-radiation exposure as possible. The fastest imaging speeds are realized by mounting a dual-coated radiographic element between a pair of fluorescent intensifying screens for imagewise exposure. About 5 percent or less of the exposing X-radiation passing through the patient is adsorbed directly by the latent image forming silver halide emulsion layers within the dual-coated radiographic element. Most of the X-radiation that participates in image formation is absorbed by phosphor particles within the fluorescent screens. This stimulates light emission that is more readily absorbed by the silver halide emulsion layers of the radiographic element. Crossover of light from one fluorescent screen to an emulsion layer on the opposite side of the support of the radiographic element results in a significant loss of image sharpness. For medical diagnostic imaging, film contrast typically ranges from about 1.8 to 3.2, depending upon the diagnostic application. Crossover is minimized. In the highest speed diagnostic dual-coated radiographic elements, those employing spectrally sensitized tabular grain emulsions, crossover typically can range up to about 25% in the absence of other crossover control measures. In fact, it is common practice to add processing solution decolorizable dye particles to reduce crossover to near zero. X-radiation exposure energies vary from about 25 kVp for mammography to about 140 kVp for chest X-rays.

Examples of radiographic element constructions for medical diagnostic purposes are provided by Abbott et al U.S. Pat. Nos. 4,425,425 and 4,425,426, Dickerson U.S. Pat. No. 4,414,310, Kelly et al U.S. Pat. Nos. 4,803,150 and 4,900,652, Tsaur et al U.S. Pat. No. 5,252,442, and *Research Disclosure*, Vol. 184, August 1979, Item 18431.

Portal radiography is used to provide images to position and confirm radiotherapy in which the patient is given a dose of high energy X-radiation (from 4 to 25 MVp) through a port in a radiation shield. The object is to line up the port with a targeted anatomical feature (typically a tumor) so the feature receives a cell killing dose of X-radiation. In localization imaging the portal radiographic element is briefly exposed to the X-radiation passing through the patient with the shield removed and then with the shield in place. Exposure without the shield provides a faint image of anatomical features that can be used as orientation references near the target (e.g., tumor) area while the exposure with the shield superimposes a second image of the port area. The exposed localization radiographic element is quickly processed to produce a viewable image and confirm that the port is in fact properly aligned with the intended anatomical target. During the above procedure patient exposure to high energy X-radiation is kept to a minimum. The patient typically receives less than 20 RADs during this procedure.

Thereafter, before the patient is allowed to move, a cell killing dose of X-radiation is administered through the port. The patient typically receives from 50 to 300 RADs during this step. Since any movement of the patient between the localization exposure and the treatment exposure can defeat the entire alignment procedure, the importance of minimizing the time elapsed during the element processing cycle is apparent. Reducing this time by even a few seconds is highly beneficial.

A second, less common form of portal radiography is the verification of the location of the cell killing exposure. Again, the object is to record enough anatomical information to confirm that the cell killing exposure was properly aligned with the targeted anatomy.

It is appreciated that the large differences in exposure times that distinguish localization and verification imaging have up to the date of this invention precluded the successful use of a single portal radiographic element to serve both applications.

Both localization and verification portal imaging have suffered from very poor image quality. Anatomical features are often faint, barely detectable or even non-detectable. This has severely restricted reliance on portal radiography.

Although excellent radiographic imaging capabilities have been realized in medical diagnostic imaging, there are fundamental differences in the imaging physics that distinguish and render nonanalogous diagnostic and portal radiographic imaging. In diagnostic imaging X-radiation photon energy of up to 140 kVp is in part absorbed within the patient and in part passed through to be absorbed in a fluorescent intensifying screen to generate light that exposes the radiographic element.

In portal imaging the multi-MVp X-radiation in part passes through the patient unabsorbed and is in part absorbed creating a secondary electron emission. A front metal intensifying screen is relied upon to intercept and absorb the secondary electron emission. This lowers minimum density and significantly enhances image sharpness. Image intensification (raising maximum density and contrast) is achieved by absorbing X-radiation and transmitting to the radiographic element electrons that are thereby generated. The much higher capability of the radiographic element to absorb electrons as compared to X-radiation produces image intensification. Besides supplying electrons that are relied upon to expose the radiographic element, the front intensifying screen further contributes to image sharpness by transmitting to a much lesser extent electrons generated by obliquely oriented (i.e., scattered) X-radiation that it receives.

In addition to the front metal intensifying screen, which is always present, a back metal intensifying screen can be employed to provide an additional source of electrons for radiographic element exposure.

Recognizing the imaging deficiencies of conventional portal radiography, Sephton U.S. Pat. 4,868,399 suggests replacing a conventional dual-coated, low contrast, and low crossover radiographic element (e.g., Kodak TL™) sandwiched between front and back metal intensifying screens with the combina- tion of a conventional high (4–8) contrast graphic arts or lithographic line film (e.g., Kodaline 2586™) and a fluorescent intensifying screen.

The Sephton portal radiographic imaging assembly failed to achieve acceptance. It suffers a number of deficiencies that place it at fundamental variance with user needs. These include (1) a greater susceptibility to false image information (e.g., the mistaking of dust or debris for anatomical information), (2) incompatibility with radiographic processors, particularly short processing cycles, and (3) an inability to accommodate a variety of exposure applications (Sephton reports only localization imaging). In addition, Sephton follows conventional diagnostic imaging practices in urging "the closest possible contact between the lead, the fluorescent layer, and the emulsion".

SUMMARY OF THE INVENTION

In one aspect the invention is directed to a process of confirming the targeting of a beam of X-radiation of from 4 to 25 MVp comprised of (a) directing the X-radiation at a subject containing features that are identifiable by differing levels of X-radiation absorption and creating a first image of X-radiation penetrating the subject in a first radiographic element, (b) placing a shield containing a portal between the subject and the source of X-radiation, directing X-radiation at the subject through the portal, and creating a second image superimposed on the first image in the first radiographic element, (c) processing the first radiographic element to obtain a viewable image from which intended targeting of the X-radiation passing through the portal in relation to the identifiable features of the subject is realized, (d) placing a second radiographic element to receive X-radiation passing through the portal in the shield and through the subject, (e) exposing the subject to X-radiation within an area defined by the portal, and (f) processing the second radiographic element to verify that exposure in step (e) was targeted as intended, wherein (g) the first and second radiographic elements are each comprised of a film support having first and second major surfaces and capable of transmitting radiation to which the radiographic element is responsive and, coated on both of the major surfaces, processing solution permeable hydrophilic colloid layers which are fully forehardened and limited to less than 45 mg/dm$^2$ of hydrophilic colloid to facilitate processing in less than 45 seconds, at least one of said layers on each major surface including light-sensitive silver halide grains capable of providing a contrast in the range of from 4 to 8 and containing less than 3 mole percent iodide, based on silver, the hydrophilic colloid layers allowing at least 30 percent crossover within a spectral region within which the silver halide grains are light-sensitive, (h) during steps (a) and (b), total X-radiation exposure is limited to 10 seconds or less, at least one metal screen capable of emitting electrons when exposed to the X-radiation beam is interposed between the X-radiation beam and the first radiographic element and at least one fluorescent intensifying screen is positioned to receive electrons from the metal screen and emit light to expose the first radiographic element, (i) during step (d), a metal screen capable of emitting electrons when exposed to the X-radiation beam is interposed between the X-radiation beam and the second radiographic element, and (j) during step (e), the X-radiation exposure is continued for at least 30 seconds.

In another aspect the invention is directed to a portal radiographic element comprised of a film support having first and second major surfaces and capable of transmitting radiation to which the radiographic element is responsive and, coated on both of the major surfaces, processing solution permeable hydrophilic colloid layers which are fully forehardened and limited to less than 45 mg/dm² of hydrophilic colloid to facilitate processing in less than 45 seconds, at least one of the layers on each major surface including light-sensitive silver halide grains capable of providing a contrast in the range of from 4 to 8 and containing less than 3 mole percent iodide, based on silver, the hydrophilic colloid layers allowing at least 30 percent crossover within a spectral region within which the silver halide grains are light-sensitive.

In another aspect the invention is directed to the combination of a metal intensifying screen and a portal radiographic element as described above.

In still another aspect the invention is directed to the combination of a pair of metal intensifying screens and a portal radiographic element as described above.

In an additional aspect the invention is directed to the combination of a metal intensifying screen, a fluorescent intensifying screen and a portal radiographic element as described above.

DESCRIPTION OF PREFERRED EMBODIMENTS

A preferred localization portal imaging configuration according to this invention, Localization Assembly A, is schematically shown as follows:

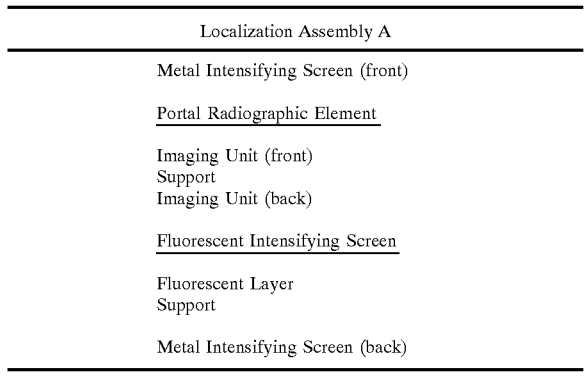

Between conventional front and back metal intensifying screens are mounted a portal radiographic element according to the invention and a conventional fluorescent intensifying screen.

The portal radiographic element is of a construction that has not previously been employed in either diagnostic or portal radiography. Its support is a conventional transparent film support, which can be clear or blue tinted. Coated on opposite sides of the support are one or more processing solution permeable hydrophilic colloid layers. To facilitate processing of the radiographic element in less than 45 seconds the hydrophilic colloid layers are fully forehardened and limited to less than 45 mg/dm² of hydrophilic colloid on each side of the support. At least one hydrophilic colloid layer on each side of the support contains light-sensitive silver halide grains chosen to facilitate processing in less than 45 seconds and to provide a contrast in the range of from 4 to 8. The portal radiographic element is constructed to allow at least 30 percent crossover of light emitted by the fluorescent screen.

During localization portal imaging the patient is briefly exposed to 4 to 25 MVp X-radiation over an area somewhat larger than the radiotherapy target area for the purpose of obtaining a discernible image of anatomy reference features outside the target area. This is immediately followed by a brief exposure through the port in the shields, to create an image of the port superimposed on the broader area first exposure. Total exposure during localization imaging is limited to 10 seconds or less, typically from 1 to 10 seconds. The object is to obtain an image that confirms or guides alignment of the port for radiotherapy, but to limit exposure to the MVp X-radiation to the extent possible. By seeing in the image the location of the port in relation to reference anatomy features, the port can be more accurately aligned with the target area, if necessary, before the longer duration radiotherapy exposure begins.

The front and back metal intensifying screens each absorb MVp X-radiation and emit electrons. The portal radiographic element itself absorbs only a very small fraction of the MVp X-radiation and the emitted electrons. The primary exposure of the portal radiographic element is provided by light emitted by the fluorescent layer of the fluorescent screen. The fluorescent layer much more efficiently than the radiographic element captures emitted electrons, resulting in light emission. The light emitted by the fluorescent screen is efficiently captured by the portal radiographic element.

It has been discovered quite unexpectedly that for portal radiography the heretofore unused combination of a single fluorescent screen and a dual coated radiographic element provides portal images that are superior to those obtained by conventional portal imaging techniques or by the failed approach of Sephton. Specifically, by going counter to the trend in diagnostic radiography of limiting crossover to low levels, it is possible to use a single fluorescent screen to expose the silver halide grains on both sides of the support. Surprisingly, for portal imaging applications a fully satisfactory image for port placement can be obtained with a dual-coated portal radiographic element and a single fluorescent intensifying screen, provided the crossover of the portal radiographic element is maintained at or above 30 percent. Substitution of a conventional low crossover dual-coated diagnostic radiographic element for the high crossover portal radiographic element contemplated by the invention results in an unsatisfactory loss in maximum density and contrast, both detrimental to obtaining a clear image of reference anatomy features. This invention, unlike the teachings of diagnostic radiography and Sephton, is actually exposing the front imaging unit as shown above with light that is supplied solely by crossover through the support.

By splitting the hydrophilic colloid coating into imaging units on opposite sides of the support, two important advantages are realized over the single sided approach taught by Sephton. First, the hydrophilic colloid per side can be limited to less than 45 mg/dm² while still obtaining suitable levels of maximum density. Preferably the hydrophilic colloid layers on opposite sides of the support are identical— i.e., the radiographic element is symmetrical. The combination of fully forehardening and limiting the coating coverages per side of hydrophilic colloid allows the portal radiographic element to be processed in less than 45 seconds in a conventional radiographic processing unit of the type routinely used for processing diagnostic radiographic elements. In other words, the elapsed delay between localization portal imaging to determine the positioning of the port and ensuing radiotherapy is now reduced to a minimum. This minimizes the risk of movement by the patient before the radiotherapy dose is administered. The additional advantage is that those engaging in portal radiotherapy can now take advantage of the same highly efficient processors that have been developed for and are in widespread use in diagnostic radiography.

Splitting the radiographic image between two imaging units addresses another problem that can arise with only a single imaging unit and a single fluores- cent screen. If only the back imaging unit were included in the portal radiographic element of localization Assembly A above, a visually distracting image of any artifact (e.g., a speck of dust or other debris) inadvertently interposed between the back imaging unit and the fluorescent layer would be superimposed on the anatomical image sought to be recorded. Using the portal radiographic elements of the invention, artifacts are less noticeable and those of small size (e.g., dust particles) are not visible.

Another advantage of the assembly shown above requires appreciation of how the screens and portal radiographic elements are assembled for exposure. The screens are mounted in a cassette. Since the screens are not consumed in imaging, they remain mounted in the cassette as successive radiographic elements are introduced for exposure during repeated use. The symmetrical, dual-coated structure of the portal radiographic element eliminates any possibility of misorientation of the radiographic element when it is inserted into the cassette. When a radiographic element contains only a single imaging unit, the element has distinct front and back sides. Failing to orient the front side to face the front metal intensifying screen produces an noticeably different image record than the correct orientation. Thus, the portal radiographic elements of the invention simplify cassette loading and eliminate a potential source of operator error.

An unexpected and highly advantageous feature of the portal radiographic elements of the invention is that the exact same portal radiographic element construction can be used for both localization portal imaging and verification portal imaging. After the operator has performed the operations described above to confirm proper placement of the port, a cassette similar to that used for localization imaging, but with the fluorescent screen and the back metal intensifying screen removed, can be loaded with another sheet of exactly the same portal radiographic element according to the invention employed for localization portal imaging.

The thus loaded cassette is then capable of providing a verification image of the actual radiotherapy exposure. During the radiotherapy exposure 4 to 25 MVp X-radiation exposures of at least 30 seconds, typically 30 to 300 seconds, are employed. If the same intensifying screens used during localization portal imaging were retained in the cassette, any portal radiographic element useful in Assembly A for localization portal imaging would be overexposed during the longer exposure of radiotherapy. Because of the longer exposure duration, the front metal intensifying screen alone or optionally in combination with the back metal intensifying screen, but without a fluorescent intensifying screen, provides sufficient exposure to provide an optimum verification image in the portal radiographic element of the invention.

The advantage to the operator, who is performing localization portal imaging and verification portal imaging in succession on each patient, is that only one portal radiographic element type needs to be employed. This simplifies stocking and eliminates any possibility of inserting an unintended type of portal radiographic element in the cassette during any given exposure.

Although photographic emulsions capable of producing extremely high contrasts, 10 or even higher, are known, the portal radiographic elements of this invention are intentionally limited to the average contrast range of from 4 to 8, preferably 4 to 6. This contrast is well above the typical maximum contrast of 3.0 exhibited by diagnostic radiographic elements. The increased contrast enhances recognition of anatomical features in the portal images obtained. However, high contrasts are avoided, since these would severely restrict the exposure latitudes of the portal radiographic films and restrict or destroy entirely the ability to employ a single portal radiographic element for varied applications. Thus, the selected contrast range markedly improves image characteristics while retaining interchangeability of localization and verification portal imaging applications as well as being able to accommodate variations in exposures within each of these categories.

Although preferred localization and verification portal assemblies have been described above, it is appreciated that varied assemblies are possible. For example, a variation on localization Assembly A is contemplated in which a light reflective element or layer is interposed between the front metal intensifying screen and the portal radiographic element. The addition of this interposed light reflective element or layer eliminates reflection of light from the front metal intensifying screen and eliminates the subtle grain pattern that many metal intensifying screens exhibit as background noise superimposed on the images recorded in the portal radiographic elements.

The exact choice of screens to be used during the localization and verification imaging steps can be varied, depending upon the output of the screens and the sensitivity of the portal radiographic element used in both exposures. Where the portal radiographic element is of somewhat lower speed or the MVp exposure during localization portal imaging tends toward minimal levels, it is specifically contemplated to insert a second fluorescent intensifying screen between the front metal intensifying screen and the portal radiographic element. In a specifically preferred localization imaging assembly, Assembly B, the back metal intensifying screen is omitted, and a second fluorescent intensifying screen is interposed between the portal radiographic element and the front metal screen. In another localization imaging assembly, Assembly C, the two metal intensifying screens of Assembly B are employed in combination with the two fluorescent intensifying screens of Assembly B, where slower speed portal radiographic elements are employed.

In the verification portal imaging assemblies it is additionally possible to include a fluorescent intensifying screen or a fluorescent layer on a metal intensifying screen to boost exposure of slower speed portal radiographic elements. However, the verification portal imaging assemblies are in all instances constructed to provide less exposing energy to the portal radiographic element per unit of time than the localization portal imaging assemblies.

To allow a single cassette construction to be employed with varied assemblies, differing in functioning elements, it is conventional practice to include within the cassette a compressible foam sheet. A plastic sheet can be used, if desired, to distribute the compressive force applied by the compressible foam sheet. This allows each assembly to be similarly compressed when the cassette is closed for exposure.

The portal radiographic elements of the invention are novel, but once the value of their unique combination of properties is appreciated, their actual construction is well within the capabilities of those skilled in the art.

Any conventional transparent radiographic or photographic film support can be employed in constructing the portal radiographic elements of the invention. It is preferred to employ a radiographic film support, since this maximizes compatibility with the rapid access radiographic film processors in which the films of the invention are intended to be processed and provides a radiographic film look and feel to the processed film. Radiographic film supports usually exhibit these specific features: (1) the film support is constructed of polyesters to maximize dimensional integrity rather than employing cellulose acetate supports as are most commonly employed in photographic elements and (2) the film supports are blue tinted to contribute the cold (blue-black) image tone sought in the fully processed films, whereas photographic films rarely, if ever, employ blue tinted supports. Radio-graphic film supports, including the incorporated blue dyes that contribute to cold image tones, are described in Research Disclosure, Item 18431, cited above, Section XII. Film Supports. Research Disclosure, Vol. 365, September 1994, Item 36544, Section XV. Supports, illustrates in paragraph (2) suitable subbing layers to facilitate adhesion of hydrophilic colloids to the support. Although the types of transparent films set out in Section XV, paragraphs (4), (7) and (9) are contemplated, due to their superior dimensional stability, the transparent films preferred are polyester films, illustrated in Section XV, paragraph (8). Poly(ethylene terephthalate) and poly (ethylene naphthenate) are specifically preferred polyester film supports.

In addition to the support the portal radiographic elements contain one or more hydrophilic colloid layers coated on each side of the support forming front and back imaging units. In the simplest possible construction each imaging unit consists of a single silver halide emulsion layer. In more typical constructions, at least one (typically one) emulsion layer is coated on each side of the support and the emulsion layer is overcoated with an interlayer and a surface overcoat. A preferred portal radiographic element layer construction is shown as PRE-I below:

| (PRE-I) |
|---|
| SURFACE OVERCOAT |
| INTERLAYER |
| EMULSION LAYER |
| SUBBING LAYER |
| TRANSPARENT FILM |
| SUBBING LAYER |
| EMULSION LAYER |
| INTERLAYER |
| SURFACE OVERCOAT |

The subbing layers and transparent film together form the support, discussed above.

The emulsion layers contain the light-sensitive silver halide relied upon for image formation. To facilitate rapid access processing the grains contain less than 3 mole percent iodide, based on total silver. The silver halide grains can take any of the following compositions: silver chloride, silver bromide, silver iodochloride, silver iodobromide, silver chlorobromide, silver bromochloride, silver iodochlorobromide, silver iodobromochloride, silver chloroiodobromide and silver iodochlorobromide. Small amounts of iodide are commonly incorporated into silver halide grains to increase their sensitivity, but in the preferred portal radiographic elements of the invention the grains are substantially free of iodide, since iodide is known to slow processing and to contribute to relatively warm image tones.

In a particularly preferred form the grains contain at least 50 mole percent chloride, based on total silver. Silver chloride exhibits the highest attainable rates of processing and is therefore specifically contemplated. It has been discovered that relatively high processing rates can be retained while increasing covering power and shifting to more desirable colder image tones by incorporating bromide as well as chloride in the grains. In an optimum balance of developability, covering power and image tone, the grains contain from 20 to 40 mole percent bromide, based on total silver. Thus silver chlorobromide emulsions are specifically preferred.

In addition to the advantages obtained by composition selection described above it is specifically contemplated to select the grains for their ability to impart contrasts in the range of from 4 to 8 to the portal radiographic elements. To achieve contrasts in this range it is contemplated to employ grains that exhibit a coefficient of variation (COV) of grain ECD of less than 20 percent and, preferably, less than 10 percent. It is preferred to employ a grain population that is as highly monodisperse as can be conveniently realized. Since monodispersity as well as development rates generally decline with increasing grain sizes, it is specifically contemplated to limit mean grain sizes to less than 0.5 $\mu$m. Grains in the mean ECD range of from 0.1 to 0.4 $\mu$m offer an optimum balance of monodispersity and speed. Generally regular (e.g. cubic or octahedral) can be obtained at higher levels of monodispersity (lower COV's) than irregular (e.g., tabular) grains in the same mean ECD ranges. Non-tabular grains, those having an average aspect ratio of less than 2, are specifically preferred. Optimally the nontabular grains have an average aspect ratio of less than 1.3. (Notice that a cube has an aspect ratio, as herein defined, that is slightly greater than 1.0.)

In addition to controlling grain size dispersity, the contrast of the portal radiographic elements are contemplated to be raised by the incorporation of one or more contrast enhancing dopants. Rhodium, cadmium, lead and bismuth are all well known to increase contrast by restraining toe development. The toxicity of cadmium has precluded its continued use. Rhodium is most commonly employed to increase contrast and is specifically preferred. Contrast enhancing concentrations are known to range from as low $10^{-9}$ mole/Ag mole. Rhodium concentrations up to $5\times10^{-3}$ mole/Ag mole are specifically contemplated. A specifically preferred rhodium doping level is from $1\times10^{-6}$ to $1\times10^{-4}$ mole/Ag mole.

A variety of other dopants are known, individually and in combination, to improve not only contrast, but other common properties, such as speed and reciprocity characteristics. Dopants capable providing shallow electron trapping sites, commonly referred to as SET dopants, are specifically contemplated. SET dopants are described in Research Disclosure, Vol. 367, November 1994, Item 36736. Iridium dopants are very commonly employed to decrease reciprocity failure. The extended exposure times of the portal radiographic elements of the invention render it highly desirable to include one or more dopants to guard against low intensity reciprocity failure, commonly referred to as LIRF. Kim U.S. Pat. No. 4,997,751, here incorporated by reference, provides a specific illustration of Ir doping to reduce LIRF. A summary of conventional dopants to improve speed, reciprocity and other imaging characteristics is provided by *Research Disclosure,* Item 36544, cited above, Section I. Emulsion grains and their preparation, sub-section D. Grain modifying conditions and adjustments, paragraphs (3), (4) and (5)

The low COV emulsions of the invention can be selected from among those prepared by conventional batch double-jet precipitation techniques. The emulsions can be prepared, for example, by incorporating a rhodium dopant during the precipitation of monodispersed emulsions of the type commonly employed in photographic reflection print elements. Specific examples of these emulsions are provided by Hasebe et al U.S. Pat. No. 4,865,962, Suzumoto et al U.S. Pat. No. 5,252,454, and Oshima et al U.S. Pat. No. 5,252,456, the disclosures of which are here incorporated by reference. A general summary of silver halide emulsions and their preparation is provided by *Research Disclosure*, Item 36544, cited above, I. Emulsion grains and their preparation.

After precipitation and before chemical sensitization the emulsions can be washed by any convenient conventional technique. Conventional washing techniques are disclosed by *Research Disclosure,* Item 36544, cited above, Section III. Emulsion washing.

The emulsions can be chemically sensitized by any convenient conventional technique. Such techniques are illustrated by *Research Disclosure,* Item 36544, IV. Chemical sensitization. Sulfur and gold sensitizations are specifically contemplated.

Both silver bromide and silver iodide have significant native sensitivity within the blue portion of the visible spectrum. Hence, when the emulsion grains contain high (>50M %, based on Ag) bromide concentrations, spectral sensitization of the grains is not essential, though still preferred. High chloride grains, particularly the specifically preferred silver bromochloride grains, possess little native sensitivity beyond the ultraviolet region of the spectrum, and are also preferably spectrally sensitized. It is specifically contemplated that one or more spectral sensitizing dyes will be absorbed to the surfaces of the grains to impart or increase their light-sensitivity. Ideally the maximum absorption of the spectral sensitizing dye is matched (e.g., within ±10 nm) to the principal emission band or bands of the fluorescent intensifying screen. In practice any spectral sensitizing dye can be employed which, as coated, exhibits a half peak absorption bandwidth that overlaps the principal spectral region(s) of emission by the fluorescent intensifying screen intended to be used with the portal radiographic element.

A wide variety of conventional spectral sensitizing dyes are known having absorption maxima extending throughout the near ultraviolet (300 to 400 nm), visible (400 to 700 nm) and near infrared (700 to 1000 nm) regions of the spectrum. Specific illustrations of conventional spectral sensitizing dyes is provided by *Research Disclosure.* Item 18431, Section X. Spectral Sensitization, and Item 36544, Section V. Spectral sensitization and desensitization, A. Sensitizing dyes.

Instability which increases minimum density in negative-type emulsion coatings (i.e., fog) can be protected against by incorporation of stabilizers, antifoggants, antikinking agents, latent-image stabilizers and similar addenda in the emulsion and contiguous layers prior to coating. Such addenda are illustrated by *Research Disclosure*, Item 36544, Section VII. Antifoggants and stabilizers, and Item 18431, Section II. Emulsion Stabilizers, Antifoggants and Antikinking Agents.

The silver halide emulsion and other layers forming the processing solution permeable imaging units on opposite sides of the support contain conventional hydrophilic colloid vehicles (peptizers and binders), typically gelatin or a gelatin derivative. Conventional vehicles and related layer features are disclosed in *Research Disclosure,* Item 36544, II. Vehicles, vehicle extenders, vehicle-like addenda and vehicle related addenda. The emulsions themselves can contain peptizers of the type set out in II. above, paragraph A. Gelatin and hydrophilic colloid peptizers. The hydrophilic colloid peptizers are also useful as binders and hence are commonly present in much higher concentrations than required to perform the peptizing function alone. The vehicle extends also to materials that are not themselves useful as peptizers. Such materials are described in II. above, C. Other vehicle components.

The elements of the invention are fully forehardened to facilitate rapid access processing. The use of any convenient conventional hardener is contemplated. Such hardeners are described in II. above, B. Hardeners.

By fully forehardening the hydrophilic colloids forming the imaging units and limiting their coating coverages the ingestion of water during processing is limited which in turn reduces the drying time required and allows dry-to-dry processing in less than 45 seconds. Water pick-up during rapid access processing, measured as the highest increase in element weight at any time during the processing cycle, is contemplated to be limited to less than 120 percent and preferably less than 115 percent. It is generally preferred to limit forehardening to permit a weight gain of at least 100 percent to insure that processing solution has an adequate opportunity to permeate the hydrophilic colloid layers.

The coating coverages of hydrophilic colloid on each side of the support are in all instances limited to less than 45 mg/dm$^2$. The hydrophilic colloid forming an emulsion layer, which is the only required layer of an imaging unit, can be limited to as little as 20 mg/dm$^2$, but is preferably at least 30 mg/dm$^2$. The minimum emulsion layer hydrophilic colloid coating coverage is limited by the silver coating coverage employed. The portal radiographic elements are contemplated to contain conventional coating coverages of silver halide to provide maximum densities in the range of from 3 to 4, the conventional aim maximum densities for diagnostic radiographic elements.

The surface overcoats are typically provided for physical protection of the emulsion layers. In addition to vehicle features discussed above the overcoats can contain various addenda to modify the physical properties of the overcoats. Such addenda are illustrated by *Research Disclosure,* Item 36544, IX. Coating physical property modifying addenda, A. Coating aids, B. Plasticizers and lubricants, C. Antistats, and D. Matting agents. The interlayers are typically thin hydrophilic colloid layers that provide a separation between the emulsion and the surface overcoat addenda. It is quite common to locate some emulsion compatible types of surface overcoat addenda, such as anti-matte particles, in the interlayers.

An increase in imaging speed can be realized by incorporating a thiaalkylene bis(quaternary ammonium) salt in at least one of (1) a processing solution permeable layer of the film (i.e., any one of the emulsion, or (2) the developer (or activator) solution used during processing. The thiaalkylene bis(quaternary ammonium) salt acts as a development accelerator and hence its activity is dependent upon being present within the emulsion layer during development. When the thiaalkylene bis(quaternary ammonium) salt is incorporated in a developer or activator, a contemplated concentration of the development accelerator is in the range of from 0.1 to 1.0 g/L, preferably from 0.2 to 0.6 g/L.

A preferred location of the thiaalkylene bis(quaternary ammonium) salt is in the emulsion layer containing hydrophilic colloid layer unit. Processing solution permeates this entire layer unit during development and hence the thiaalkylene bis(quaternary ammonium) salt diffuses into the emulsion layer with the developer or activator solution, if it is not initially coated directly within the emulsion layer. Useful thiaalkylene bis(quaternary ammonium) salt concentrations in the hydrophilic colloid layer unit containing the emulsion layer are contemplated to range from 0.02 to 1.0 mg/dm$^2$, preferably from 0.05 to 0.60 mg/dm$^2$.

When the thiaalkylene bis(quaternary ammonium) salt is incorporated in a hydrophilic colloid layer unit on the back side of the support, it is necessary that the salt diffuse from the back side layer unit into the developer and then into the hydrophilic colloid layer unit containing the emulsion layer. In this instance somewhat higher concentrations are required than when the salt is incorporated directly in the emulsion layer containing hydrophilic colloid layer unit to achieve comparative effects.

In a preferred form the thiaalkylene bis-(quaternary ammonium) salt satisfies the formula:

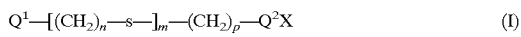

$$Q^1-[(CH_2)_n-S-]_m-(CH_2)_p-Q^2 X \qquad (I)$$

where m is an integer of from 1 to 3, n and p are independently integers of from 1 to 6, $Q^1$ and $Q^2$ are ammonio groups, and X represents the ion or ions necessary to provide charge neutrality.

Typical ammonio groups include simple acyclic groups, such as illustrated by the formula:

$$\begin{array}{c} R^1 \\ | \\ R^2-N- \\ | \\ R^3 \end{array} \quad + \qquad (II)$$

where $R^1$, $R^2$ and $R^3$ are independent hydrocarbon groups each containing from 1 to 10 (preferably 1 to 6) carbon atoms. To facilitate solubility and mobility in processing solutions it is preferred to limit the number of carbon atoms or to substitute the hydrocarbon atoms with polar substituents, such as carboxy, sulfonyl, carbamoyl, amido, sulfamoyl or sulfonamido groups. Preferred hydrocarbon groups are phenyl, alkylphenyl, phenylalkyl and alkyl groups. It is specifically preferred to limit the total number of carbon atoms in any one ammonio group to 10 or less.

In an alternative preferred form $R^1$ and $R^2$ can together complete a membered ring. Where $R^1$ and $R^2$ together form an alkylene group, typically the alkylene group contains from 4 to 10 carbon atoms. In most instances $R^1$ and $R^2$ are chosen to complete a 5 or 6 membered ring. For example, $R^1$ and $R^2$ can together complete an N—$R^3$-pyrrolio, N—$R^3$-pyrrolinio, N—$R^3$-pyrazinio, N—$R^3$-morpholinio, N—$R^3$-piperidinio or N—$R^3$-piperazinio ring.

It is specifically contemplated to employ ammonio groups illustrated by the following formula:

$$\begin{array}{c} | \\ R^4-N=R^5 \\ + \end{array} \qquad (III)$$

where $R^4$ and $R^5$ together complete a five or six membered ring. For example, the ammonio group can be an N-2H-pyrroleninio or N-pyridinio group.

In heterocyclic ammonio groups and particularly aromatic heterocylic ammonio groups it is not necessary that the point of attachment to the linking thiaalkylene group be at the site of the quaternized nitrogen atom. From example, ammonio groups such as 4-(N-methylpyrindinio) and N'-(N-methylpyrazinio) ammonio groups are specifically contemplated.

The charge balancing counterions can be chosen from any of the anions commonly found in silver halide emulsion layers, including halide ions (e.g., fluoride, chloride, bromide), hydroxide, phosphate, sulfate, nitrate, tetrafluoroborate, p-toluenesulfonate, and perchlorate. Anions compatible with silver halide emulsions can be used interchangeably without affecting the activity of the development accelerator.

The following are illustrations of specific thiaalkylene bis(quaternary ammonium) salts:

Q-1  N,N'-[1,8-(3,6-dithiaoctylene)]bis(1-methylpiperidinium) p-toluenesulfonate;

Q-2  N,N'-[1,10-(3,8-dithiadecylene)]bis(1-methylpiperidinium) p-toluenesulfonate;

Q-3  N,N'-[1,12-(3,10-dithiadodecylene)]bis(1-methylpiperidinium) p-toluenesulfonate;

Q-4  N,N'-[1,8-(3,6-dithiaoctylene)]bis(1-methylmorpholinium) p-toluenesulfonate;

Q-5  N,N'-[1,8-(3,6-dithiaoctylene)]bis(trimethylammonium) p-toluenesulfonate;

Q-6  N,N'-[1,8-(3,6-dithiaoctylene)]bis(diethylmethylammonium) p-toluenesulfonate;

Q-7  N,N'-[1,8-(3,6-dithiaoctylene)]bis(1,7-heptylenemethylammonium) p-toluenesulfonate;

Q-8  N,N'-[1,8-(3,6-dithiaoctylene)]bispyridinium tetrafluoroborate;

Q-9  N,N'-[1,8-(3,6-dithiaoctylene)]bis(4-dimethylaminopyridinium) bromide;

Q-10  N,N'-[1,8-(3,6-dithiaoctylene)]bis(3-formylpyridinium) bromide;

Q-11  N,N'-[1,8-(3,6-dithiaoctylene)]bis(4-methylpyridinium) bromide;

Q-12  N,N'-[1,8-(3,6-dithiaoctylene)]bis[3-(4-methylphenylsulfonamido)pyridinium] bromide;

Q-13  N,N'-[1,8-(3,6-dithiaoctylene)]bis[4-(5-nonyl)pyridinium] bromide;

Q-14  N,N'-[1,8-(3,6-dithiaoctylene)]bis(3-pentamido)pyridinium) bromide;

Q-15  N,N'-[1,8-(3,6-dithiaoctylene)]bis(3-propylcarbamoyl)pyridinium) bromide;

Q-16  N,N'-[1,8-(3,6-dithiaoctylene)]bis(1-methylmorpholinium) p-toluenesulfonate;

Q-17 N,N'-[1,13-(2,12-dihydroxy-3,6-dithiatridecylene)]bis(trimethylammonium) p-toluenesulfonate;

Q-18 N,N'-[1,13-(2,12-dihydroxy-3,6-dithiatridecylene)]bis(dibutylmethylammonium) p-toluenesulfonate;

Q-19  4,4'-[1,11-(3,6,9-trithiaundecyl)]bis(N-methylpyridinium) p-toluenesulfonate;

Q-20  N,N'-[1,11-(3,6,9-trithiaundecyl)]bis[4-(dimethylamino)pyridinium] bromide;

Q-21  4,4'-[1,8-(3,6-dithiaoctyl)]bis(N-methylpyridinium) perchlorate;

Q-22 2,2'-[1,8-(3,6-dithiaoctyl)]bis(N-methylpyridinium) perchlorate;

Q-23 N,N'-[1,19-(7,13-dithianonadecyl)]bis(2-methylpyridinium) p-toluenesulfonate;

The fluorescent intensifying screens can take any convenient conventional form. High resolution fluorescent intensifying screens, such as, for example, those employed in mammography, are unnecessary, since the object is simply to provide images with identifiable anatomical features, not the fine detail required for diagnostics. The fluorescent layers can take any of the forms of those found in intermediate to high speed fluorescent intensifying screens and typically the fluorescent intensifying screens contain a reflective or transparent film support, preferably the former. If a transparent support is employed in Assembly A above, reflection of light from the back metal intensifying screen can be used to increase the amount of light transmitted to the portal radiographic element. If a reflective (e.g., white) support is incorporated in the fluorescent intensifying screen, even a higher proportion of emitted light will reach the portal radiographic element. Examples of conventional, useful fluorescent intensifying screens are provided by *Research Disclosure,* Item 18431, cited above, Section IX. X-Ray Screens/Phosphors, and Bunch et al U.S. Pat. No. 5,021,327 and Dickerson et al U.S. Pat. Nos. 4,994,355, 4,997,750, and 5,108,881, the disclosures of which are here incorporated by reference. The fluorescent layer contains phosphor particles and a binder, optimally additionally containing a light scattering material, such as titania. Higher emission efficiencies are realized with phosphors such as calcium tungstate ($CaWO_4$) niobium and/or rare earth activated yttrium, lutetium or gadolinium tantalates, and rare earth activated rare earth oxychalcogenides and halides.

The rare earth oxychalcogenide and halide phosphors are preferably chosen from among those of the following formula:

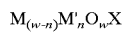 (IV)

wherein

M is at least one of the metals yttrium, lanthanum, gadolinium or lutetium,

M' is at least of the rare earth metals, preferably dysprosium, erbium, europium, holmium, neodymium, praseodymium, samarium, terbium, thulium, or ytterbium, X is a middle chalcogen (S, Se or Te) or halogen, n is 0.002 to 0.2, and w is 1 when X is halogen or 2 when X is chalcogen.

In Assembly A the fluorescent intensifying screen is shown interposed between the portal radiographic element and the back metal intensifying screen. Alternatively the fluorescent intensifying screen can be interposed between the portal radiographic element and the front metal intensifying screen. When two fluorescent intensifying screens are employed, they can be independently selected, being the same or different in composition and emission efficiencies. The high crossover between the imaging units of the portal radiographic element allows each fluorescent intensifying screen to expose the front and back imaging units.

The metal intensifying screens can take any convenient conventional form. While the metal intensifying screens can be formed of many different types of materials, the use of metals is most common, since metals are most easily fabricated as thin foils, often mounted on radiation transparent backings to facilitate handling. Convenient metals for screen fabrication are in the atomic number range of from 22 (titanium) to 82 (lead). Metals such as copper, lead, tungsten, iron and tantalum have been most commonly used for screen fabrication with lead and copper in that order being the most commonly employed metals.

The metal foils typically range from 0.1 to 2 mm in thickness when employed as a front screen. A preferred front screen thickness range for lead is from about 0.1 to 1 mm and for copper from 0.25 to 2 mm. Generally the higher the atomic number, the higher the density of the metal and the greater its ability to absorb MVp X-radiation.

The back metal intensifying screens can be constructed of the same materials as the front intensifying screens. In the case of the back metal intensifying screen, the only advantage to be gained by limiting their thickness is reduction in overall cassette weight. Since a back metal intensifying screen is not essential, there obviously is no minimum essential thickness, but typically the back metal intensifying screen is at least as thick as the front metal intensifying screen with which it is used when both are of the same composition. Generally the thickness of the back metal intensifying screen is determined on the basis of convenience of fabrication and handling and the weight it adds to the cassette assembly.

Widely employed metal intensifying screen combinations include (a) front and back lead intensifying screens and (b) front copper and back lead intensifying screens. The latter combination is preferred, since it reduces assembly weight and has been demonstrated to facilitate better imaging under at least some selected conditions of exposure.

Instead of employing separate metal and fluorescent intensifying screens, it is possible to integrate both functions into a single element by coating a fluorescent layer onto one or both of the metal intensifying screens. A preferred arrangement of this type is shown below as Assembly B:

---

Localization Assembly B

---

Metal Intensifying Screen (front)

Portal Radiographic Element

Imaging Unit (front)
Support
Imaging Unit (back)

Integrated Intensifying Screen

Fluorescent Layer
Metal Intensifying Screen (back)

---

Localization Assembly B can be converted to a verification imaging assembly simply by removing the integrated intensifying screen. Another option for localization imaging is to replace the front metal intensifying screen with an integrated intensifying screen that is used in addition to or as an alternative to the back integrated intensifying screen.

EXAMPLES

In the examples all coating coverages are in units of $mg/dm^2$, except as otherwise indicated.

Example 1

The following radiographic elements were constructed for comparison in localization portal imaging:

The following elements were constructed to demonstrate the advantages of the invention and to compare alternatives that might be suggested by current state of the art. All elements employed a blue tinted poly(ethylene terephthalate) film support having a thickness of 178 μm. All of the hydrophilic colloid layers were hardened with bis(vinylsulfonylmethyl)ether, at a level of 2.4 percent by weight, based on total weight of gelatin.

PRE-1A (Invention)

A portal radiographic element exhibiting a crossover of 40% and an average contrast of >4.0 satisfying the requirements of the invention was constructed to have the following structure:

| (PRE-1A) |
| --- |
| SURFACE OVERCOAT |
| INTERLAYER |
| EMULSION LAYER |
| SUPPORT |
| EMULSION LAYER |
| INTERLAYER |
| SURFACE OVERCOAT |

| Surface Overcoat | Coverage |
| --- | --- |
| Gelatin | 3.4 |
| Methyl methacrylate (matte beads) | 0.14 |
| Carboxymethyl casein | 0.57 |
| Colloidal silica | 0.57 |
| polyacrylamide | 0.57 |
| Chrome alum | 0.025 |
| Resorcinol | 0.058 |
| Whale oil lubricant | 0.15 |

| Interlayer | Coverage |
| --- | --- |
| Gelatin | 3.4 |
| Carboxymethyl casein | 0.57 |
| Colloidal silica | 0.57 |
| Polyacrylamide | 0.57 |
| Chrome alum | 0.025 |
| Resorcinol | 0.058 |
| Nitron | 0.044 |

| Emulsion Layer | Coverage | |
| --- | --- | --- |
| AgBr$_{30}$Cl$_{70}$ (ECD 0.34 μm, Rh doped) | 18.3 | |
| Gelatin | 21.5 | |
| Antifoggant-1 | 2.1 | mg/Agmole |
| Sensitizing Dye-1 | 0.35 | |
| Sensitizing Dye-2 | 1.41 | |
| Surfactant | 1.7 | |
| Hydroquinone | 0.47 | |
| Latex Polymer-1 | 1.28 | |
| APMT | 0.006 | |
| Chelating Agent-1 | 0.11 | |

Rh doped
  $6.9 \times 10^{-5}$ gram atoms Rh per Ag mole
Antifoggant-1
  2-Carboxy-4-hydroxy-6-methyl-1,3,3A,7-tetraazaindene
Sensitizing Dye-1
  3-Carboxymethyl-5-[(3-methyl-2(3H)-thiazolinylidene)isopropylidene]rhodanine
Sensitizing Dye-2
  3-Ethyl-5-[1-(4-sulfobutyl)-4(1H)-pyridyliene)rhodanine
Latex Polymer-1
  Poly(methyl acrylate-co-2-acrylamido-2-methylpropane sulfonic acid, sodium salt-co-2-acetoacetoethyl methacrylate) (89.6:3.7:6.7 wt. ratio)
AMPT
  1-(3-Acetamidophenyl)-5-mercaptotetrazole Chelating Agent-1
  Ethylenediaminetetraacetic acid, disodium salt

PRE-1S (A Control)

This portal radiographic element was constructed identically to the Kodaline 2586™ graphic arts film employed by Sephton U.S. Pat. No. 4,868,399, except that the blue tinted support described above was employed to facilitate comparability and transport through the rapid access processor. The film exhibited the following structure:

| (PRE-1S) |
| --- |
| SURFACE OVERCOAT |
| INTERLAYER |
| EMULSION LAYER |
| SUPPORT |
| PELLOID LAYER |
| INTERLAYER |
| SURFACE OVERCOAT |

The surface overcoat and interlayers were identical to those of PRE-1A. The single emulsion layer contained the sum of the ingredients of the two emulsion layers of PRE-1A. The pelloid layer exhibited the following structure:

| Pelloid Layer | Coverage |
| --- | --- |
| Gelatin | 48.0 |
| Dye-3 | 0.24 |
| Dye-4 | 0.37 |
| Dye-5 | 0.13 |

Dye-3
  Bis[3-methyl-1-(p-sulfophenyl)-2-pyrazolin-5-one-(4H)] methineoxonol
Dye-4
  4-[4-(N,N-dimethylamino)phenyltrimethine]-3-methyl-1-p-sulfophenylpyrazolin-5-one-(4H) triethylamine (a.k.a. acid violet)
Dye-5
  Bis[3-methyl-1-(p-sulfophenyl)-2-pyrazolin-5-one-(4H)] pentamethineoxonol

PRE-1C (A Control)

A conventional dual-coated diagnostic radiographic element having a crossover of 24% was provided for comparison. The diagnostic radiographic element exhibited the same overall layer arrangement as PRE-1A. The surface overcoats and interlayers were identical to those of PRE-1A. The composition of the emulsion layer is shown below:

| Emulsion Layer | Coverage | |
| --- | --- | --- |
| AgBr T-Grains ™ | 22.0 | |
| Gelatin | 32.0 | |
| Antifoggant-1 | 2.1 | mg/Agmole |
| Potassium nitrate | 1.8 | |
| Ammonium hexachloropalladate | 0.0022 | |
| Sorbitol | 0.53 | |
| Glycerin | 0.57 | |

-continued

| Emulsion Layer | Coverage |
| --- | --- |
| Potassium bromide | 0.14 |
| Resorcinol | 0.44 |

AgBr T-Grains™

This was a spectrally sensitized emulsion of the type disclosed by Abbott et al U.S. Pat. No. 4,425,425. That is, the silver bromide grains were high aspect ratio tabular grains. Greater than 50 percent of total grain projected area was accounted for by tabular grains having an average thickness of 0.13 $\mu$m and an average ECD of 2.0 $\mu$m. The emulsion was spectrally sensitized with 400 mg/Ag mole of anhydro-5,5'-dichloro-9-ethyl-3,3'-bis(3-sulfopropyl) oxacarbo-cyanine hydroxide, followed by the addition of 300 mg/Ag mole of potassium iodide.

Cassette Assemblies

The following screen-cassette were assembled for comparison of localization portal imaging capabilities of varied films:

Cassette L

This cassette was chosen to illustrate a conventional cassette of the type presently used in localization portal imaging. Its intensifying screens consisted of a 1.0 mm copper front screen and a 0.25 mm lead back screen.

Cassette L1S

This cassette was similar to Cassette L, except that the back lead screen was replaced by a fluorescent intensifying screen, Screen W, described below.

Screen W

This fluorescent intensifying screen is commercially available as Lanex™ fast back. It consists of a terbium activated gadolinium oxysulfide phosphor having a median particle size of 7 $\mu$m coated on a white pigmented poly (ethylene terephthalate) film support in a Permuthane™ polyurethane binder at a total phosphor coverage of 13.3 g/dm$^2$ at a phosphor to binder ratio of 19:1.

Performance

The imaging performance of the radiographic elements in the cassettes is summarized below in Table I.

TABLE I

| Assembly | Rel. Speed | γ | % XO | % Dryer | Artifacts |
| --- | --- | --- | --- | --- | --- |
| PRE-1C/L | 100 | 1.6 | NR | 70% | Low |
| PRE-1C/L1S | 13,200 | 2.3 | 24 | 70% | Low |
| PRE-1S/L1S | 29 | 5.3 | NR | >100% | High |
| PRE-1A/L1S | 45 | 4.6 | 40 | 40% | Low |

When the conventional dual-coated diagnostic radiographic element PRE-1C was mounted in Cassette L between copper and lead intensifying screens, given an exposure to MVp X-radiation representative of localization portal imaging, and processed using a rapid access processor, a low contrast image was obtained that provided a poor definition of simulated anatomical features. The film was processable in less than 45 seconds and exhibited a low noticeability of artifacts in the final image, which necessarily followed from its poor definition of anatomical features. Crossover was not relevant (NR), since the metal intensifying screens did not emit light.

When a fluorescent intensifying screen was added to the assembly, replacing the back lead intensifying screen, the speed of the assembly became excessively high. This high level of speed was incompatible with using the film for either localization or verification portal imaging. Thus, diagnostic radiographic element PRE-1C had utility for only localization portal imaging with metal intensifying screens.

When PRE-1S was substituted for PRE-1C in Cassette L1S, improved contrast was observed, but the film could not be processed in less than 45 seconds. It passed through the processor without being fully dried, which is the result of the excessively high coating of hydrophilic colloid on one side of the support and this in turn being a function of the silver coated on the one side of the support. Artifacts were quite noticeable in processed film. This demonstrates the incompatibility of the Sephton approach to localization portal imaging using rapid access processing techniques. Further, the prominence of artifacts in the images was objectionable.

When the localization portal imaging radiographic element of the invention, PRE-1A, was substituted for the PRE-1S radiographic element, improved imaging characteristics were obtained and the radiographic element required only 40 percent of the drying cycle in the rapid access processor to be fully dried. Thus, taking imaging properties (e.g. contrast and the observability of anatomical features), the relatively low visibility of artifacts, and the rapid access processing capability, PRE-1S, satisfying the requirements of the invention, exhibited overall properties superior to those of either the diagnostic radiographic element or the Sephton localization portal radiographic element. A further advantage of PRE-1A over PRE-1S is that the latter contained a dyed pelloid layer requiring operator care in orienting the radiographic element for imaging, whereas PRE-1A has identical front and back imaging unit coatings and hence entirely obviates any need for front and back side orientations during cassette assembly.

In Table II below the comparative performance of control PRE-1S and invention PRE-1A using one (L1S) or two (L2S) fluorescent intensifying screens is shown.

TABLE II

| Assembly | Rel. Speed | γ |
| --- | --- | --- |
| PRE-1S/L1S | 34 | 5.3 |
| PRE-1S/L2S | 37 | 5.5 |
| PRE-1A/L1S | 45 | 4.5 |
| PRE-1A/L2S | 78 | 7.8 |

From Table II it can be seen that radiographic element PRE-1A, satisfying the requirements of the invention, demonstrated an additional speed gain and contrast enhancement when a second fluorescent intensifying screen was added, whereas the performance of PRE-1S remained essentially similar, with one or two fluorescent intensifying screens mounted in the cassette.

Rapid access processing of film samples was accomplished using a Kodak 480 RA X-Omat™ processor adjusted for the following processing cycle:

| | |
|---|---|
| Development | 11.1 sec., 37° C. |
| Fixing | 9.4 sec., 35° C. |
| Wash | 7.6 sec., 35° C. |
| Drying | 12.2 sec., 60° C. |
| Total time | 40.3 sec. |

The developer composition was as follows:

| Component | g/L |
|---|---|
| Hydroquinone | 32.0 |
| 4-Hydroxymethyl-4-methyl-1-phenyl-pyrazolidone | 6.0 |
| Potassium bromide | 2.25 |
| 5-Methylbenzotriazole | 0.125 |
| Sodium sulfite | 160.0 |
| pH 10.35 | |
| Water to 1 L | |

The fixer composition was as follows:

| Component | g/L |
|---|---|
| Ammonium thiosulfate | 131.0 |
| Sodium thiosulfate | 15.0 |
| Sodium bisulfate | 180.0 |
| Boric acid | 25.0 |
| Acetic acid | 10.0 |
| pH 4.9 | |
| Water to 1 L | |

Percent drying in Table I was determined by feeding an exposed film sample flashed to result in an density of 1.0 into the rapid access processor. As the film just began to exit the processor, the processor was stopped and the film was removed from the processor for examination. On wet portions of the film roller marks are visible. A 100% dryer rating indicates that the film had not dried. That is, roller marks were observed on the portion of the film exiting the processor. When the film dried within the processor, the percentage of the dryer rollers the film had to traverse before roller marks on the film disappeared is noted as % dryer.

Crossover was measured according to the procedure described by Abbott et al U.S. Pat. No. 4,425,425.

Relative speeds in this example were measured by placing the indicated film/cassette combination beneath a 10 cm stack of acrylic plastic slabs and irradiating with 6 MVp X-radiation from a Varian Clinac 1800™ therapy X-ray machine. The X-ray beam incident to the acrylic slab stack was 24.5×24.5 cm in size. For each cassette/film combination a series of film samples were exposed with the X-Ray machine's Monitor unit setting (relative exposure) being adjusted by a factor of two for each successive film exposure. After processing as described above, diffuse transmission visual optical densities of all films were measured with an X-rite Model 310™ photographic densitometer having a 3 mm diameter measuring aperture. From a graph of the measured optical densities versus the relative exposures, in monitor units, the number of monitor units required to produce an optical density of 1.0 above base + fog density was determined for each film/cassette combination. The reciprocal of the monitor units thus determined were then multiplied by a constant to give a relative speed of 100 for the PRE-1C/L film-cassette assembly, which is commonly used for localization portal imaging. The speed of the PRE-1C/L1S film-cassette assembly was estimated. The lowest possible exposure (1.0 Monitor unit) from the X-Ray machine produced an optical density of 3.72, which is near the film's maximum density. Thus this film-cassette combination was much too fast for use in the X-ray machine. For the Table II relative speeds the multiplication constant was chosen to provide a relative speed of 34 for the PRE-1S/L1S film-screen combination.

Values of average gradient for the films exposed to light from the fluorescent intensifying screen W were determined using an automated intensity scale (inverse square law) X-ray sensitometer device. With this device, each film, while in contact with a single Screen W, was given a sequential stepped series of 26 X-ray exposure levels with 0.10 $\log_{10}$ exposure increments. The X-ray exposure time for each exposure was 3.0 seconds. The X-ray intensity, and hence the fluorescent screen brightness, was adjusted to give the required exposure steps by changing the distance from the film-cassette assembly to the X-ray tube focal spot. The inverse square of the distance was used as a measure of relative exposure. After each exposure the film-cassette assembly was translated behind an aperture in a lead plate mounted to intercept the X-ray beam to present a new unexposed region of film for the next exposure step in the series. The X-ray tube had a tungsten target and was operated at 80 kVcp (constant potential). The X-ray beam was filtered by a 0.5 mm thick copper plate plus a 2.0 mm thick aluminum plate.

The average gradient of the film-cassette assembly PRE-1C/L exposed directly to ionizing radiation, as opposed to light from a fluorescent intensifying screen, was obtained from time scale sensitometry done with a X-Ray beam from a tungsten target X-Ray tube operated at 320 kVcp. The X-Ray beam was filtered by a 11.6 mm thick copper plate. The film was exposed while in a cassette having a 0.13 mm front lead intensifying screen and a 0.25 mm back lead intensifying screen. The cassette was translated in a stepwise fashion behind an aperture in a lead plate placed in the X-ray beam at a distance of 1.0 m from the X-ray tube target. A total of 21 exposure levels, in 0.15 $\log_{10}$ exposure increments, were given to the film by varying the exposure times as required from 1.0 to 1000 seconds. After the films were processed as described above, the relative exposure values required for the average contrast calculation were determined from graphs of the film optical density, measured as described above, plotted versus the $\log_{10}$ relative exposure.

EXAMPLE 2

This example demonstrates the suitability of PRE-1A for verification portal imaging in addition to its suitability for localization portal imaging, demonstrated in Example 1. Further this example compares the performance of PRE-1A in verification imaging to that of PRE-V1, a film now in commercial use for verification portal imaging.

PRE-1V (Control)

A verification portal radiographic element was constructed to have the following structure:

| (PRE-IV) |
|---|
| SURFACE OVERCOAT |
| INTERLAYER |
| EMULSION LAYER |
| SUPPORT |
| EMULSION LAYER |

-continued (PRE-IV)

INTERLAYER
SURFACE OVERCOAT

| Surface Overcoat | Coverage |
|---|---|
| Gelatin | 6.97 |
| Methyl methacrylate (matte beads) | 2.95 |
| Resorcinol | 1.8 |

| Interlayer | Coverage |
|---|---|
| Gelatin | 6.97 |
| Resorcinol | 2.1 |
| Nitron | 1.8 |

| Emulsion Layer | Coverage | |
|---|---|---|
| $AgI_{1.5}Br_{98.5}$ (ECD 0.42 μm) | 21.2 | |
| Gelatin | 50.62 | |
| Antifoggant-1 | 1.8 | mg/Agmole |
| Potassium nitrate | 1.0 | |
| Ammonium hexachloropalladate | 0.0022 | |
| Maleic acid hydrazide | 0.0087 | |
| Potassium bromide | 0.14 | |

The Support was identical to that of the other radiographic elements described above. Formaldehyde at the level of 1 percent, based on the total weight of gelatin, was employed as a hardener.

Cassette V

This cassette was similar to Cassette L, previously described, except that the back lead screen was replaced with a 0.4 mm poly(ethylene terephthalate) sheet. Thus, this cassette contained only a 1.0 mm copper front screen.

Performance

The imaging performance of varied radiographic elements and cassettes is shown in Table III.

TABLE III

| Assembly | Rel. Speed | γ |
|---|---|---|
| PRE-1C/L | 4110 | 1.6 |
| PRE-1V/L | 169 | 1.6 |
| PRE-1V/V | 100 | 1.6 |
| PRE-1A/L | 43 | 1.9 |

From Table II it can be seen that the localization portal radiographic element now in commercial use, PRE-1C, is much too fast for verification portal imaging. The verification portal radiographic element now in commercial use, PRE-1V, is useful with either the L or V Cassettes. PRE-1A, which produced the highest quality images overall in localization portal imaging also provides a useful image for verification imaging. Thus, PRE-1A is capable of replacing both PRE-1C and PRE-1V, each of which are restricted to a single type portal imaging. Further, it should be noticed that PRE-1A is producing a superior image in terms of contrast as compared to conventional radiographic elements PRE-1C and PRE-1V.

The data for Table III was collected from samples that received a standard (<90 seconds) processing cycle in a Kodak RP X-Omat ™ processor, model M6A-N, M6B or M35A. The developer composition was as follows:

| Component | g/L |
|---|---|
| Hydroquinone | 30.0 |
| 1-Phenyl-3-pyrazolidone | 1.5 |
| KOH | 21.0 |
| $NaHCO_3$ | 7.5 |
| $K_2SO_3$ | 44.2 |
| $Na_2S_2O_5$ | 12.6 |
| NaBr | 35.0 |
| 5-Methylbenzotriazole | 0.06 |
| Glutaraldehyde | 4.9 |
| pH | 10 |
| Water to 1 L | |

The film samples would have exhibited essentially the same speed and contrast if the processing conditions of Example 1 had been employed.

Average contrast was determined as was previously described in Example 1.

Average speed was determined using the same 6 MVp X-ray machine as in Example 1. Relative speeds using the V and L cassettes were determined using a human chest phantom. The relative speed of the PRE-1V/V film-cassette assembly was assigned a relative value of 100, and the relative speeds of the other film-cassette assemblies were referenced to this speed.

The invention has been described in detail with particular reference to preferred embodiments thereof, but it will be understood that variations and modifications can be effected within the spirit and scope of the invention.

What is claimed is:

1. A process of confirming the targeting of a beam of X-radiation of from 4 to 25 MVp comprising (a) directing the X-radiation at a subject containing features that are identifiable by differing levels of X-radiation absorption and creating first image of X-radiation penetrating the subject in a first radiographic element, (b) placing a shield containing a portal between the subject and the source of X-radiation, directing X-radiation at the subject through the portal, and creating a second image superimposed on the first image in the first radiographic elements.

(c) processing the first radiographic element to obtain a viewable image from which intended targeting of the X-radiation passing through the portal in relation to the identifiable features of the subject is realized, (d) placing a second radiographic element to receive X-radiation passing through the portal in the shield and through the subject, (e) exposing the subject to X-radiation within an area defined by the portal, and (f) processing the second radiographic element to verify that exposure in step (e) was targeted as intended,

WHEREIN (g) the first and second radiographic elements are each comprised of a film support having first and second major surfaces and capable of transmitting radiation to which the radiographic element is responsive and, coated on both of the major surfaces, processing solution permeable hydrophilic colloid layers which are fully forehardened and limited to less than 45 mg/dm² of hydrophilic colloid to facilitate processing in less than 45 seconds, at least one of said layers on each major surface including light-sensitive silver halide grains capable of providing a contrast of the radiographic element in the range of from 4 to 8 and containing less than 3 mole percent iodide, based on silver, said processing solution permeable hydrophilic colloid layers allowing at least 30 percent crossover within a spectral region within which the silver halide grains are light-sensitive, (h) during steps (a) and (b), total X-radiation exposure is limited to 10 seconds or less, at least one metal screen capable of emitting electrons when exposed to the X-radiation beam is interposed between the X-radiation beam and the first radiographic element and at least one fluorescent intensifying screen is positioned to receive electrons from the metal screen and emit light to expose the first radiographic element, (i) during step (d), a metal screen capable of emitting electrons when exposed to the X-radiation beam is interposed between the X-radiation beam and the second radiographic element, and (j) during step (e), the X-radiation exposure is continued for at least 30 seconds.

2. A process of confirming the targeting of a beam of X-radiation of from 4 to 25 MVp comprising (a) directing the X-radiation at a subject containing features that are identifiable by differing levels of X-radiation absorption and creating a first image of X-radiation penetrating the subject in a first radiographic element, (b) placing a shield containing a portal between the subject and the source of X-radiation, directing X-radiation at the subject through the portal, and creating a second image superimposed on the first image in the first radiographic element, (c) processing the first radiographic element to obtain a viewable image from which intended targeting of the X-radiation passing through the portal in relation to the identifiable features of the subject is realized, (d) placing a second radiographic element to receive X-radiation passing through the portal in the shield and through the subject, (e) exposing the subject to X-radiation within an area defined by the portal, and (f) processing the second radiographic element to verify that exposure in step (e) was targeted as intended,

WHEREIN (g) the first and second radiographic elements are identically constructed and are each comprised of a film support having first and second major surfaces and capable of transmitting radiation to which the radiographic element is responsive and, coated on both of the major surfaces, processing solution permeable hydrophilic colloid layers which are fully forehardened and limited to less than 45 mg/dm$^2$ of hydrophilic colloid to facilitate processing in less than 45 seconds, at least one of said layers on each major surface including light-sensitive silver halide grains capable of providing a contrast of the radiographic element in the range of from 4 to 8 and containing less than 3 mole percent iodide, based on silver, said processing solution permeable hydrophilic colloid layers allowing at least 30 percent crossover within a spectral region within which the silver halide grains are light-sensitive, (h) during steps (a) and (b), total X-radiation exposure is limited to 10 seconds or less, at least one metal screen capable of emitting electrons when exposed to the X-radiation beam is interposed between the X-radiation beam and the first radiographic element and at least one fluorescent intensifying screen is positioned to receive electrons from the metal screen and emit light to expose the first radiographic element, (i) during step (d), a metal screen capable of emitting electrons when exposed to the X-radiation beam is interposed between the X-radiation beam and the second radiographic element, and (j) during step (e), the X-radiation exposure is continued for at least 30 seconds.

3. A process of confirming the targeting of a beam of X-radiation of from 4 to 25 MVp comprising (a) directing the X-radiation at a subject containing features that are identifiable by differing levels of X-radiation absorption and creating a first image of X-radiation penetrating the subject in a first radiographic element, (b) placing a shield containing a portal between the subject and the source of X-radiation, directing X-radiation at the subject through the portal, and creating a second image superimposed on the first image in the first radiographic element, (c) processing the first radiographic element to obtain a viewable image from which intended targeting of the X-radiation passing through the portal in relation to the identifiable features of the subject is realized, (d) placing a second radiographic element to receive X-radiation passing through the portal in the shield and through the subject, (e) exposing the subject to X-radiation within an area defined by the portal, and (f) processing the second radiographic element to verify that exposure in step (e) was targeted as intended,

WHEREIN (g) the first and second radiographic elements are each comprised of a film support having first and second major surfaces and capable of transmitting radiation to which the radiographic element is responsive and, coated on both of the major surfaces, processing solution permeable hydrophilic colloid layers which are identical and which are fully forehardened and limited to less than 45 mg/dm$^2$ of hydrophilic colloid to facilitate processing in less than 45 seconds, at least one of said layers on each major surface including light-sensitive silver halide grains capable of providing a contrast of the radiographic element in the range of from 4 to 8 and containing less than 3 mole percent iodide, based on silver, said processing solution permeable hydrophilic colloid layers allowing at least 30 percent crossover within a spectral region within which the silver halide grains are light-sensitive, (h) during steps (a) and (b), total X-radiation exposure is limited to 10 seconds or less, at least one metal screen capable of emitting electrons when exposed to the X-radiation beam is interposed between the X-radiation beam and the first radiographic element and at least one fluorescent intensifying screen is positioned to receive electrons from the metal screen and emit light to expose the first radiographic element, (i) during step (d), a metal screen capable of emitting electrons when exposed to the X-radiation beam is interposed between the X-radiation beam and the second radiographic element, and (j) during step (e), the X-radiation exposure is continued for at least 30 seconds.

4. A process according to claim 1, 2 or 3 wherein during steps (a) and (b) two fluorescent intensifying screens are positioned on opposites sides of and in contact with the first radiographic element.

5. A process according to claim 1, 2 or 3 wherein during step (e) two metal screens are positioned on opposite sides of and in contact with the second radiographic element.

6. A portal radiographic element comprised of
a film support having first and second major surfaces and capable of transmitting radiation to which the radiographic element is responsive and, coated on both of the major surfaces,
processing solution permeable hydrophilic colloid layers which are fully forehardened and limited to less than 45 mg/dm$^2$ of hydrophilic colloid to facilitate processing in less than 45 seconds, at least one of said layers on each major surface including light-sensitive silver halide grains capable of providing a contrast of the radiographic element in the range of from 4 to 8 and containing less than 3 mole percent iodide, based on silver,
the hydrophilic colloid layers allowing at least 30 percent crossover within a spectral region within which the silver halide grains are light-sensitive.

7. A portal radiographic element comprised of
a film support having first and second major surfaces and capable of transmitting radiation to which the radiographic element is responsive and, coated on both of the major surfaces,
identical processing solution permeable hydrophilic colloid layers which are fully forehardened and limited to less than 45 mg/dm$^2$ of hydrophilic colloid to facilitate processing in less than 45 seconds, at least one of said layers on each major surface including light-sensitive silver halide grains capable of providing a contrast of the radiographic element in the range of from 4 to 8 and containing less than 3 mole percent iodide, based on silver,
the hydrophilic colloid layers allowing at least 30 percent crossover within a spectral region within which the silver halide grains are light-sensitive.

8. A portal radiographic element according to claim 6 or 7 wherein the film support is a transparent film support.

9. A portal radiographic element according to claim 6 or 7 wherein the silver halide grains have an average equivalent circular diameter of less than 0.5 µm and an average aspect ratio of less than 2.0.

10. A portal radiographic element according to claim 9 wherein the silver halide grains have an average aspect ratio of less than 1.3.

11. A portal radiographic element according to claim 6 or 7 wherein the silver halide grains have a coefficient of variation of grain size of less than 20 percent.

12. A portal radiographic element according to claim 11 wherein the silver halide grains have a coefficient of variation of grain size of less than 10 percent.

13. A portal radiographic element according to claim 6 or 7 wherein the silver halide grains contain rhodium as a contrast enhancing dopant.

14. A portal radiographic element according to claim 6 or 7 wherein the hydrophilic colloid layers contain at least 20 mg/dm$^2$ hydrophilic colloid per side.

15. A portal radiographic element according to claim 14 wherein the hydrophilic colloid layers contain at least 30 mg/dm$^2$ hydrophilic colloid per side.

16. A portal radiographic element according to claim 6 or 7 wherein forehardening limits weight gain to from 100 to 120 percent during processing in less than 45 seconds.

17. A portal radiographic element according to claim 16 wherein forehardening limits weight gain to from 100 to 115 percent during processing in less than 45 seconds.

18. A portal radiographic element comprised of
a blue tinted transparent film support having first and second major surfaces and, coated on both of the major surfaces,
identical processing solution permeable hydrophilic colloid layers which are, to facilitate processing in less than 45 seconds, forehardened to allow a maximum weight gain of the radiographic element of from 100 to 120 percent during processing in a reference processing cycle and contain from 30 to 45 mg/dm$^2$ of hydrophilic colloid, at least one of said layers on each major surface including rhodium doped light-sensitive silver chlorobromide grains having an average equivalent circular diameter in the range of from 0.1 to 0.4 µm and a coefficient of variation of grain equivalent circular diameter of less than 20 percent to provide a contrast of the radiographic element in the range of from 4 to 6,
the processing solution permeable hydrophilic colloid layers allowing from 30 to 50 percent crossover within a spectral region within which the silver halide grains are light-sensitive,
the reference processing cycle being as follows:

| development | 11.1 sec., 37° C. |
|---|---|
| fixing | 9.4 sec., 35° C. |
| wash | 7.6 sec., 35° C. |
| drying | 12.2 sec., 60° C. | where development occurs in the following developer:

| hydroquinone | 32.0 g/L |
|---|---|
| 4-hydroxymethyl-4-methyl-1-phenyl-pyrazolidone | 6.0 g/L |
| potassium bromide | 2.25 g/L |
| 5-methylbenzotriazole | 0.125 g/L |
| sodium sulfite | 160.0 g/L |
| pH 10.35 | |
| water to 1 L | | fixing occurs in the following fixer:

| ammonium thiosulfate | 131.0 g/L |
|---|---|
| sodium thiosulfate | 15.0 g/L |
| sodium bisulfate | 180.0 g/L |
| boric acid | 25.0 g/L |
| acetic acid | 10.0 g/L |
| pH 3.9–4.5 | |
| water to 1 L | | and washing is conducted in deionized water.

19. A combination of a portal radiographic element according to claim 6, 7 or 18 and a metal intensifying screen mounted between the portal radiographic element and a source of exposing X-radiation.

20. A combination according to claim 19 additionally including a second metal intensifying screen mounted to receive X-radiation that has passed through the portal radiographic element.

21. A combination according to claim 19 additionally including a first fluorescent intensifying screen mounted adjacent the portal radiographic element.

22. A combination according to claim 19 additionally including a fluorescent layer coated on a surface of the metal intensifying screen oriented toward the portal radiographic element, the fluorescent layer being capable of being stimulated by electrons to emit light.

23. A combination according to claim 21 in which said first fluorescent intensifying screen is mounted between the metal intensifying screen and one major surface of the portal radiographic element and a second fluorescent intensifying screen is mounted adjacent another major surface of the portal radiographic element.

* * * * *